United States Patent [19]
Boden et al.

[11] Patent Number: 5,227,367
[45] Date of Patent: Jul. 13, 1993

[54] OXYPENTAMETHYLINDANE CARBOXALDEHYDES, METHODS FOR PREPARING SAME, ORGANOLEPTIC USES THEREOF AND COSMETIC AND PHARMACEUTICAL COMPOSITIONS CONTAINING THEM

[75] Inventors: Richard M. Boden, Ocean; Joseph A. McGhie, South Orange; Braja D. Mookherjee, Holmdel; Myrna L. Hagedorn, Edison, all of N.J.

[73] Assignee: International Flavors & Fragrances Inc., New York, N.Y.

[21] Appl. No.: 992,013

[22] Filed: Dec. 17, 1992

[51] Int. Cl.⁵ .................................. A61K 7/46
[52] U.S. Cl. ......................... 512/17; 568/440
[58] Field of Search ............. 568/327, 440; 512/17

[56] References Cited
U.S. PATENT DOCUMENTS

| | | | |
|---|---|---|---|
| 3,509,215 | 4/1970 | Wood et al. | 512/17 |
| 4,001,330 | 1/1977 | Curran | 568/327 |
| 4,568,782 | 2/1986 | Pognotta et al. | 568/327 |
| 4,908,349 | 3/1990 | Gonzenbach | 512/17 |
| 5,095,152 | 3/1992 | Frank | 568/440 |

Primary Examiner—James H. Reamer
Attorney, Agent, or Firm—Arthur L. Liberman

[57] ABSTRACT

Described are oxypentamethylindane carboxaldehydes defined according to the generic structure:

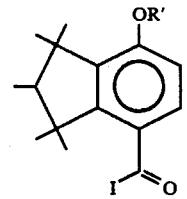

wherein R' represents a hydrogen or methyl, methods for preparing same, organoleptic uses thereof and cosmetic and pharmaceutical compositions containing them. The oxypentamethylindane carboxaldehydes particularly are useful in perfumery and as U.V. absorbers in sun screen compositions.

12 Claims, 17 Drawing Sheets

FIG.4-A
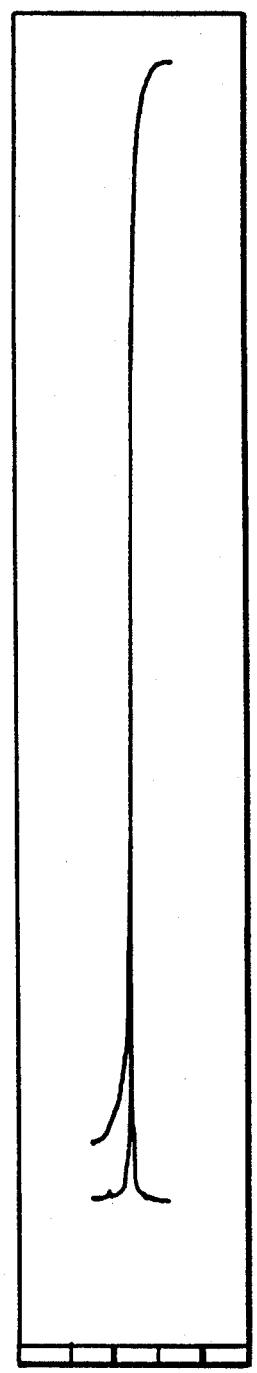
11.3  11.2
PPM
FIG.4-B
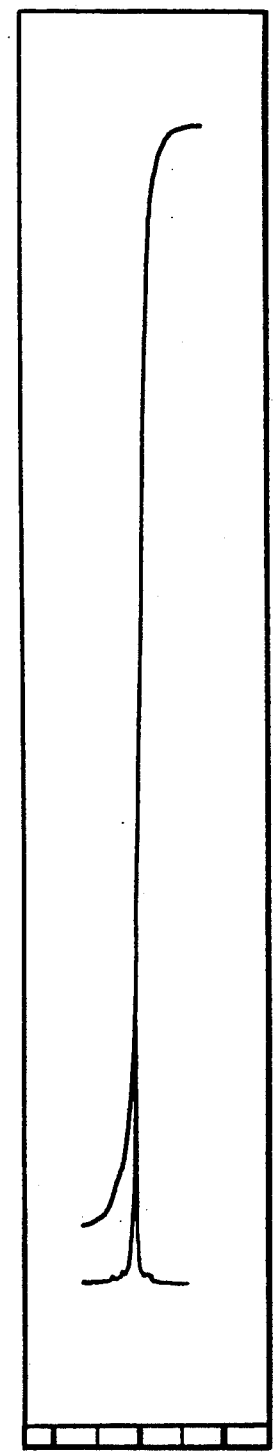
9.8  9.6
PPM

FIG.4-C
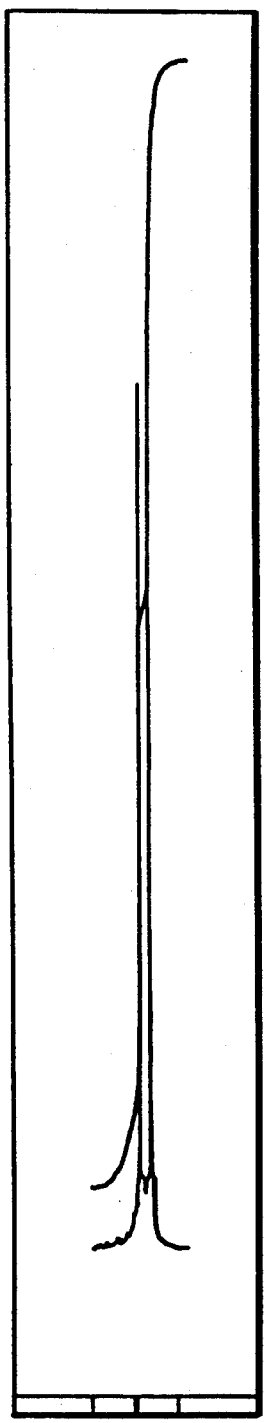
7.4
PPM
FIG.4-D
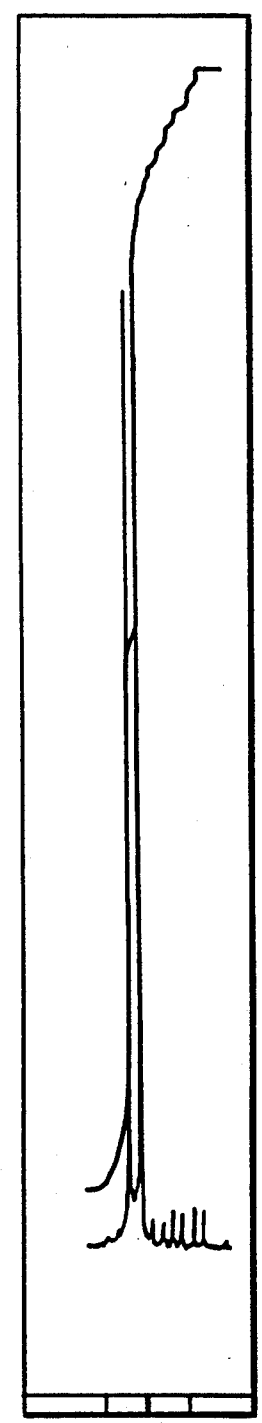
6.8
PPM

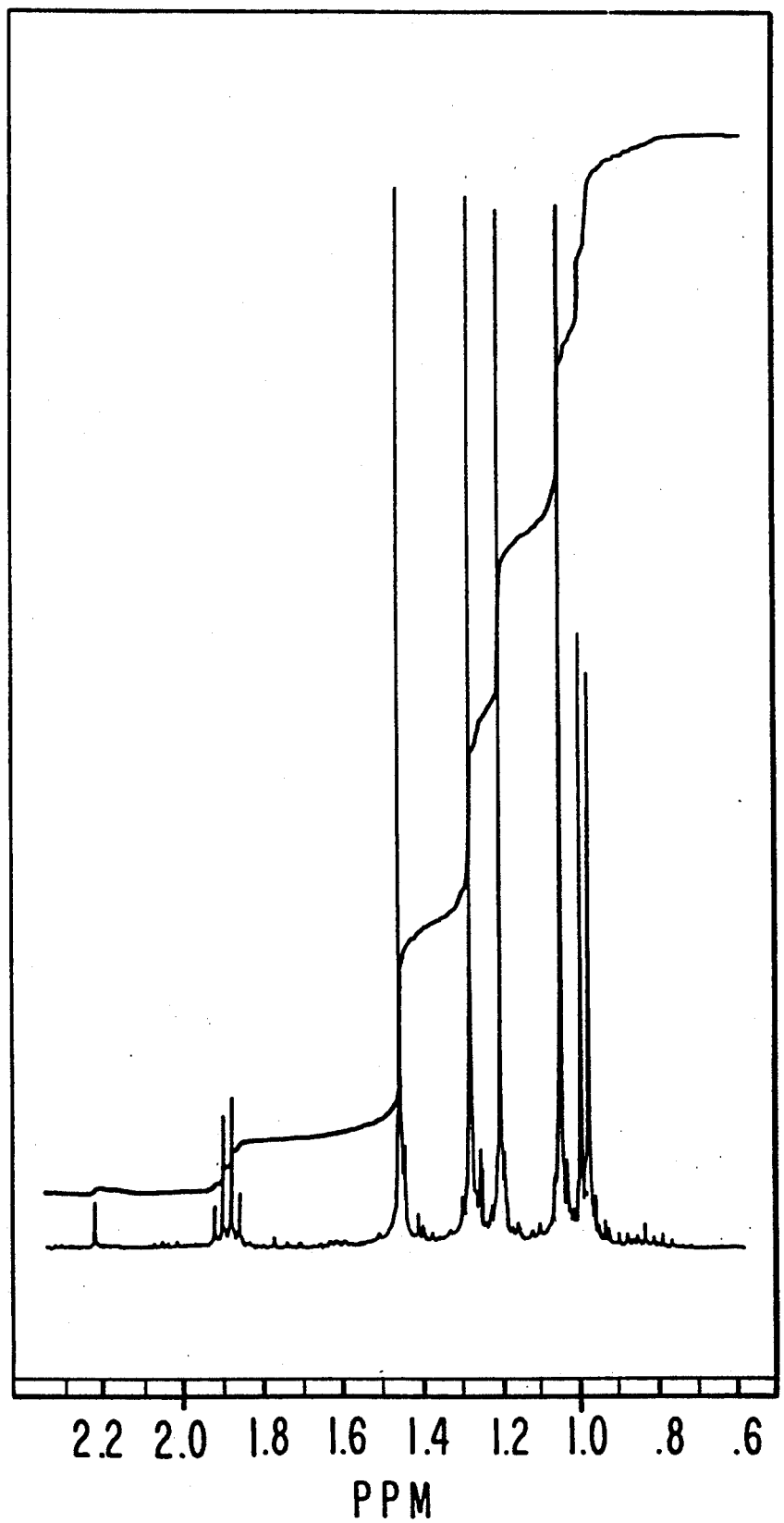
FIG.4-E

FIG.8-A
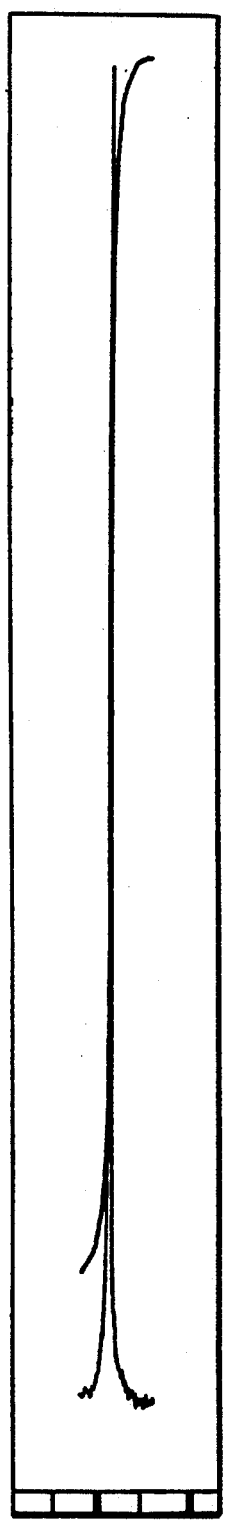
11.3  11.2
PPM
FIG.8-B
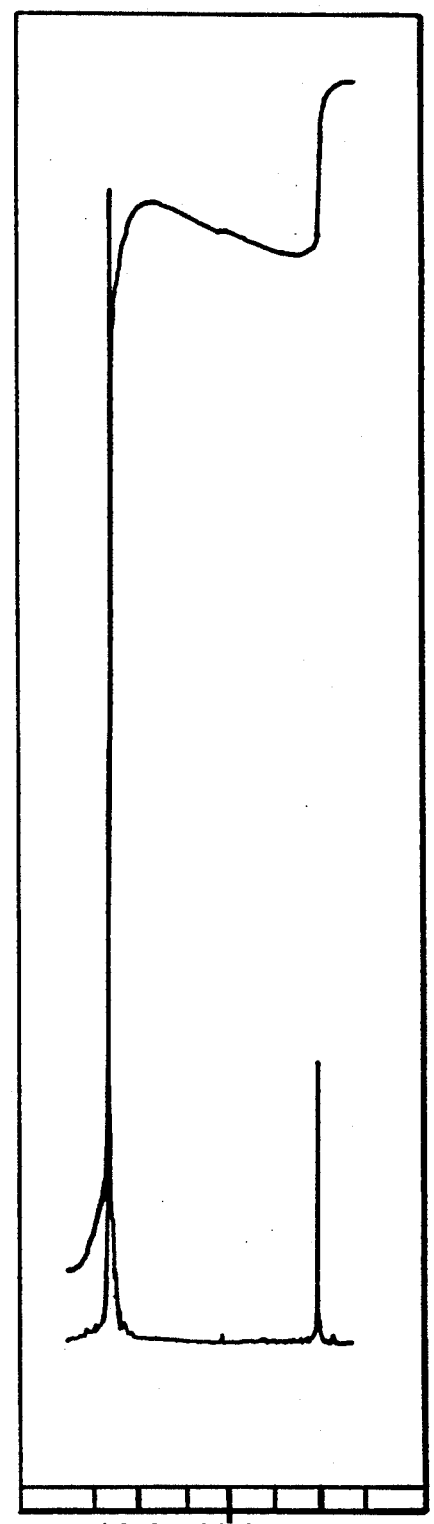
10.2  10.0  9.8
PPM

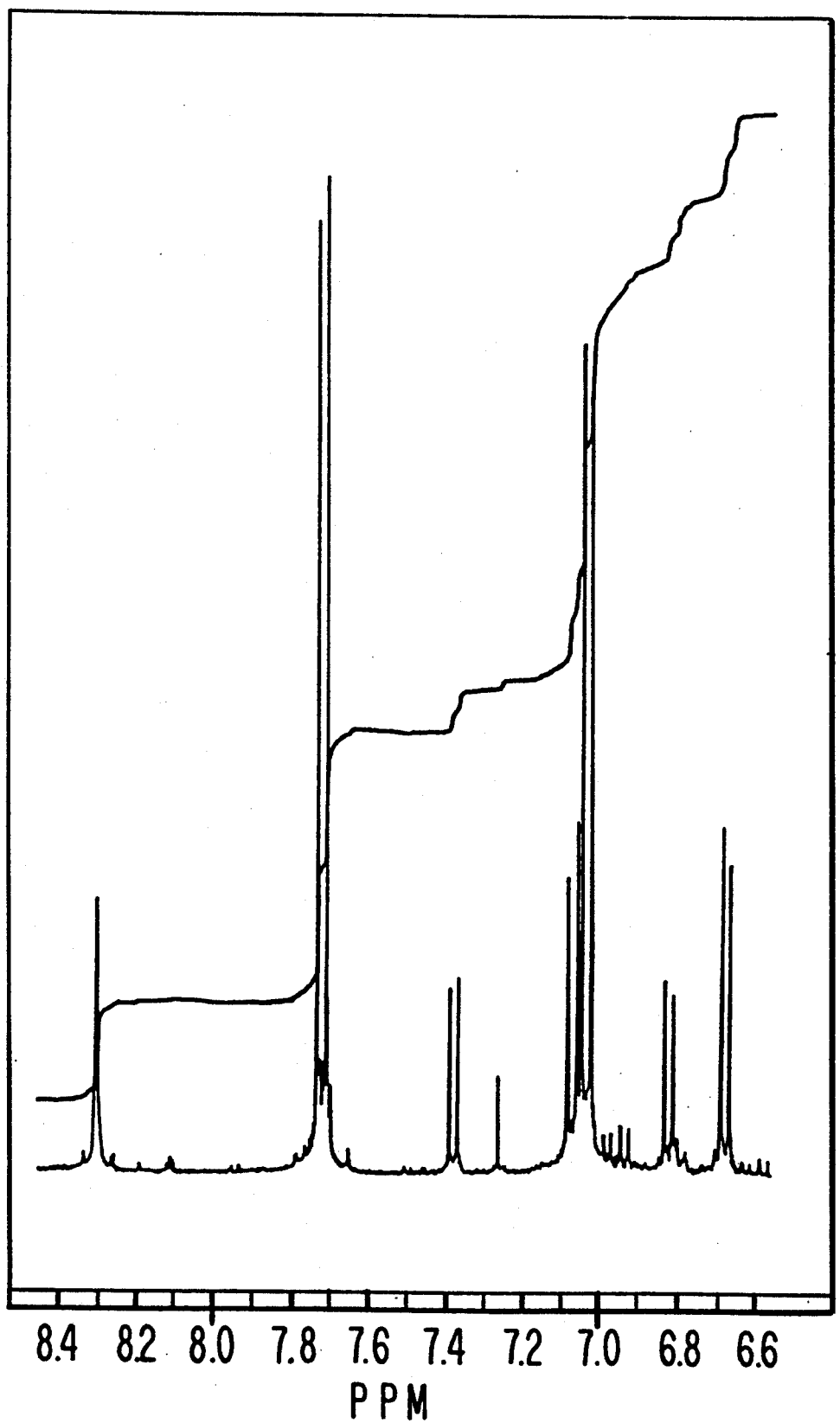
FIG. 8-C

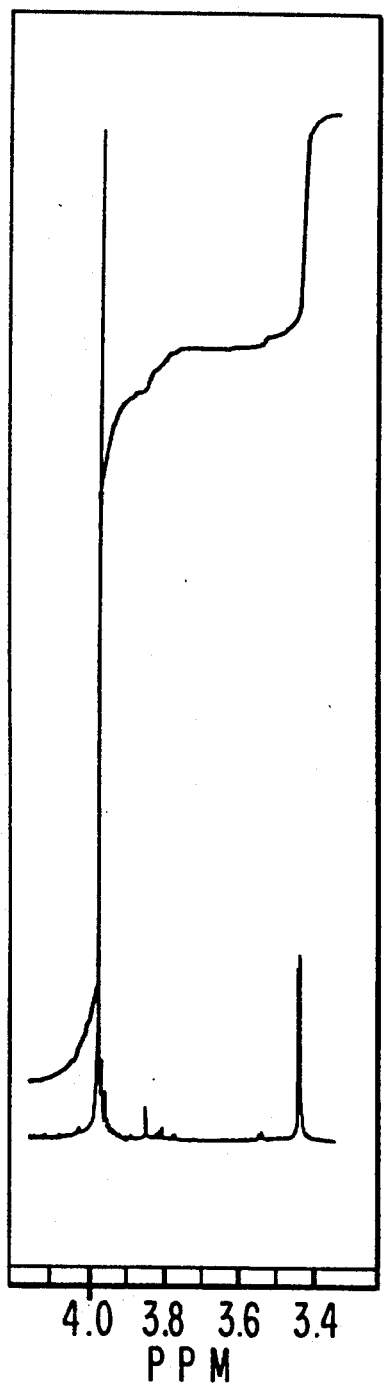
FIG.8-D
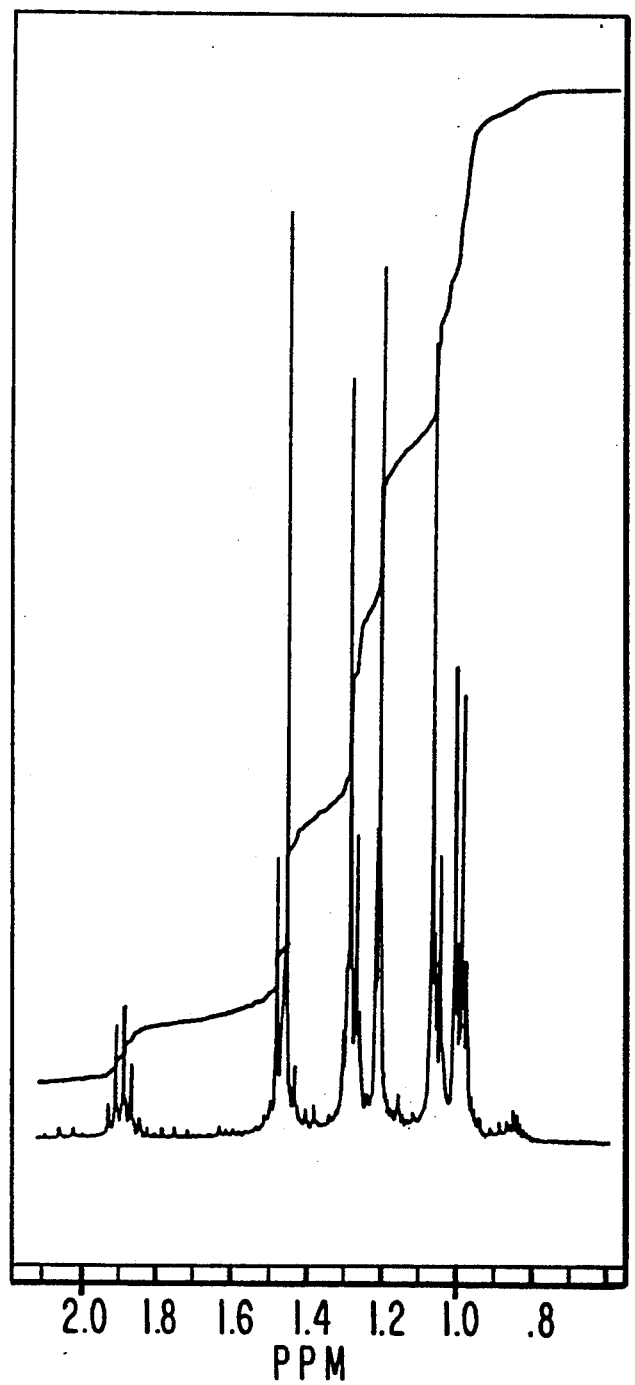
FIG.8-E

FIG.12-A
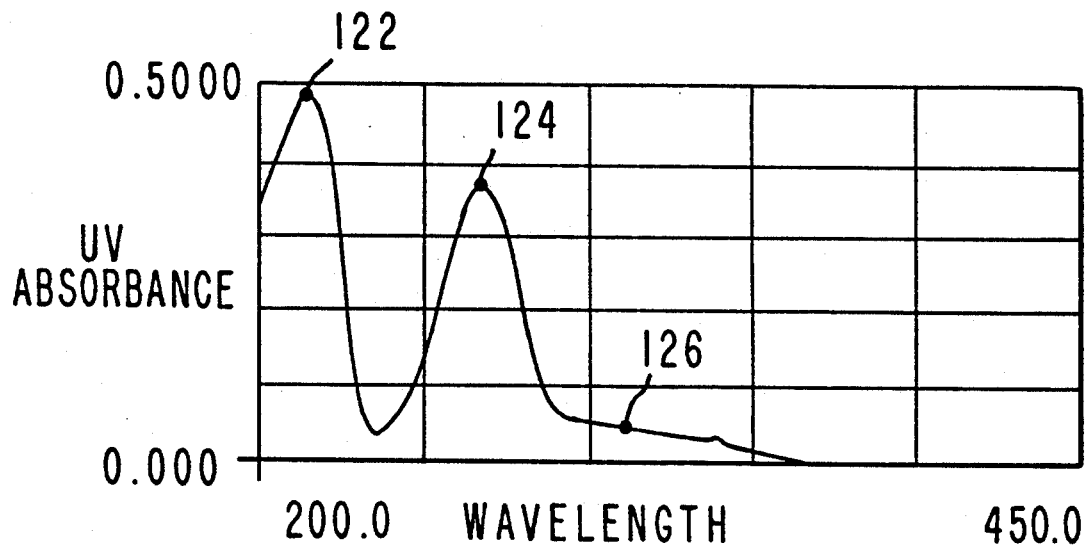
FIG.12-B
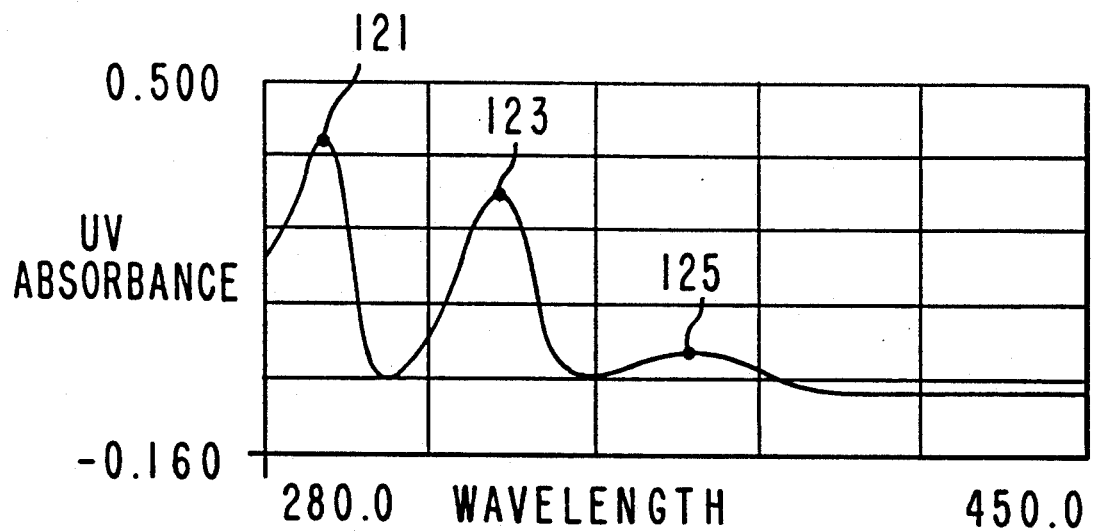

OXYPENTAMETHYLINDANE CARBOXALDEHYDES, METHODS FOR PREPARING SAME, ORGANOLEPTIC USES THEREOF AND COSMETIC AND PHARMACEUTICAL COMPOSITIONS CONTAINING THEM

BACKGROUND OF THE INVENTION

Our invention relates to oxypentamethylindane carboxaldehydes defined according to the generic structure:

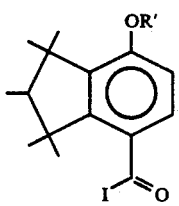

wherein R' is hydrogen or methyl as well as organoleptic uses thereof, processes for preparing such oxypentamethylindane carboxaldehydes and cosmetic and pharmaceutical compositions containing such oxypentamethylindane carboxaldehydes.

Chemical compounds which can provide musky, woody, rose, herbaceous and sweet aromas with leathery undertones are highly desirable in the art of perfumery. Many of the natural materials which provide such fragrances and contribute such desired nuances to perfumery compositions are high in cost, unobtainable at times, vary in quality from one batch to another and/or are generally subject to the usual variations of natural products. Furthermore, chemical compounds which are not only good ultraviolet light absorbers and therefore useful in sun screen compositions and are also aesthetically pleasing insofar as their aromas are concerned are highly sought after.

Compounds defined according to the generic structure:

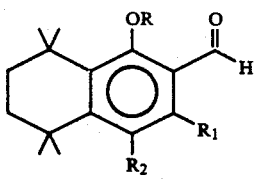

are shown to have musk aromas in U.S. Pat. Nos. 4,476,040; 4,605,778 and Canadian Patent 1,190,564 where R is hydrogen or methyl and $R_1$ and $R_2$ are hydrogen, methyl or ethyl. However, these same documents indicate that the compounds having the structures:

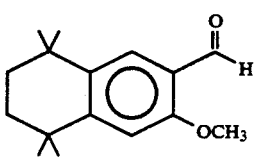

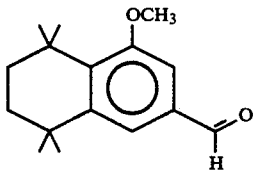

are "odorless" whereas the compound having the structure:

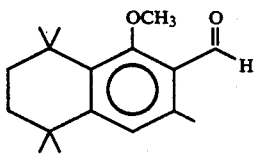

has an intense musk aroma.

Accordingly, the perfumery properties of such bicyclic compounds bearing a carbonyl moiety and an oxy moiety are highly unpredictable.

Maignan, et al, U.S. Pat. No. 5,043,482 discloses compounds having the structure:

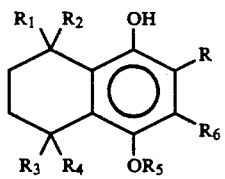

wherein $R_1$, $R_2$, $R_3$ and $R_4$ represent lower alkyl; $R_5$ and $R_6$ represent hydrogen or lower alkyl; R represents hydrogen, $C_1$-$C_{18}$ alkyl, $C_2$-$C_{18}$ alkyl substituted by one or more hydroxyl groups, $C_3$-$C_{18}$ alkenyl, $C_2$-$C_{18}$ acyl, benzyl, benzoyl, carboxyl and carboxylic salts of an alkali or alkaline earth metal or of an organic amine as antioxidants in cosmetic compositions and in pharmaceutical compositions for the preventive treatment of cutaneous inflammations and allergies or certain forms of cancer.

Nothing is expressly or implicitly stated in the Maignan, et al reference that compounds such as the oxypentamethylindane carboxaldehydes of our invention are good ultraviolet light absorbers to protect skin and hair.

Nothing in the prior art sets forth the advantages of the oxypentamethylindane carboxaldehydes of our invention either explicitly or implicitly.

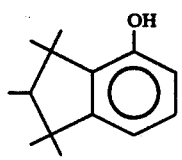

(Conditions: Carboxwax column programmed at 100°-220° C. at 8° C. per minute).

Figure 1:
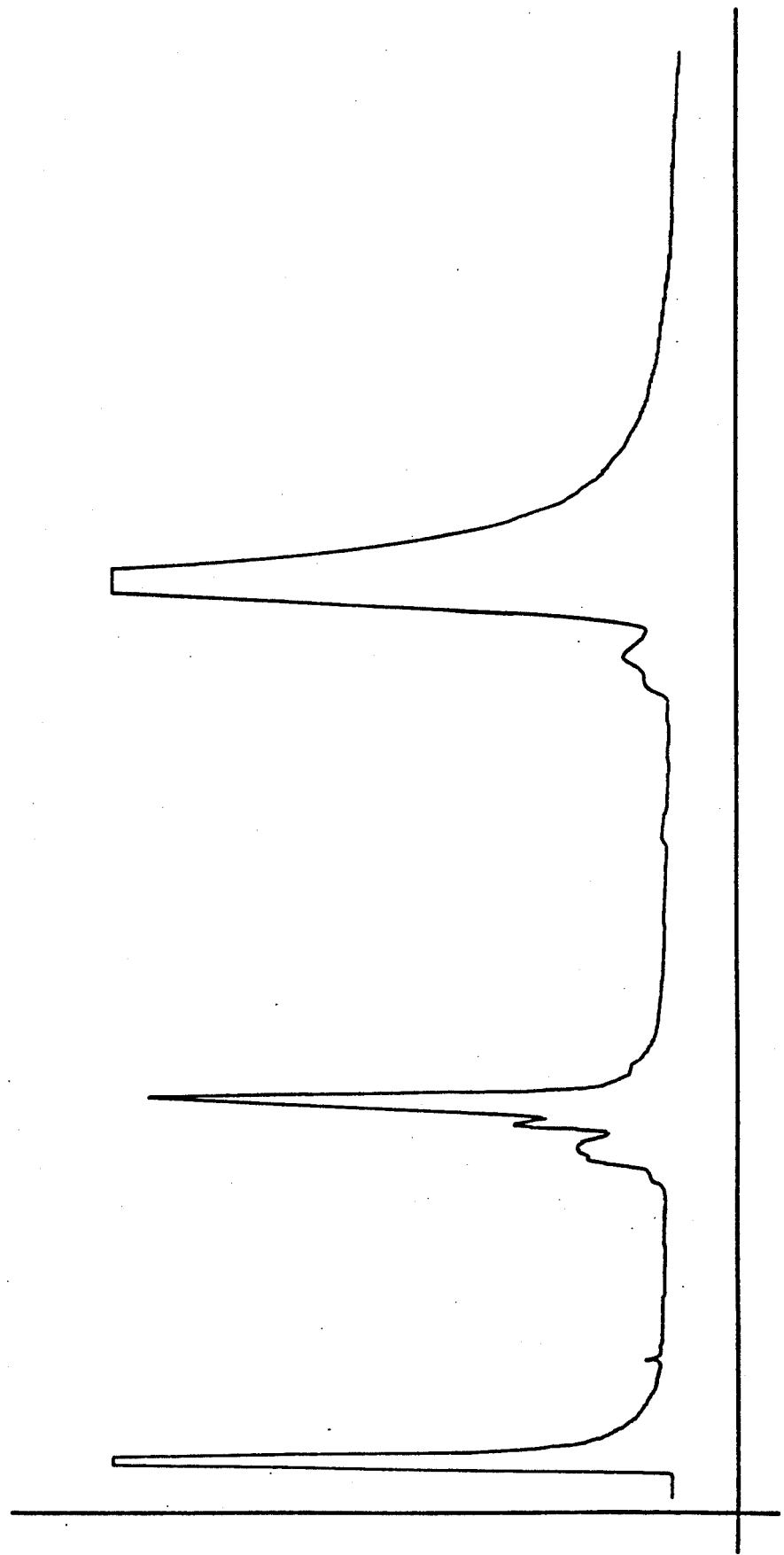
FIG. 1 is the GC spectrum for the starting material for use in Example I containing the compound having the structure.
Figure 2:
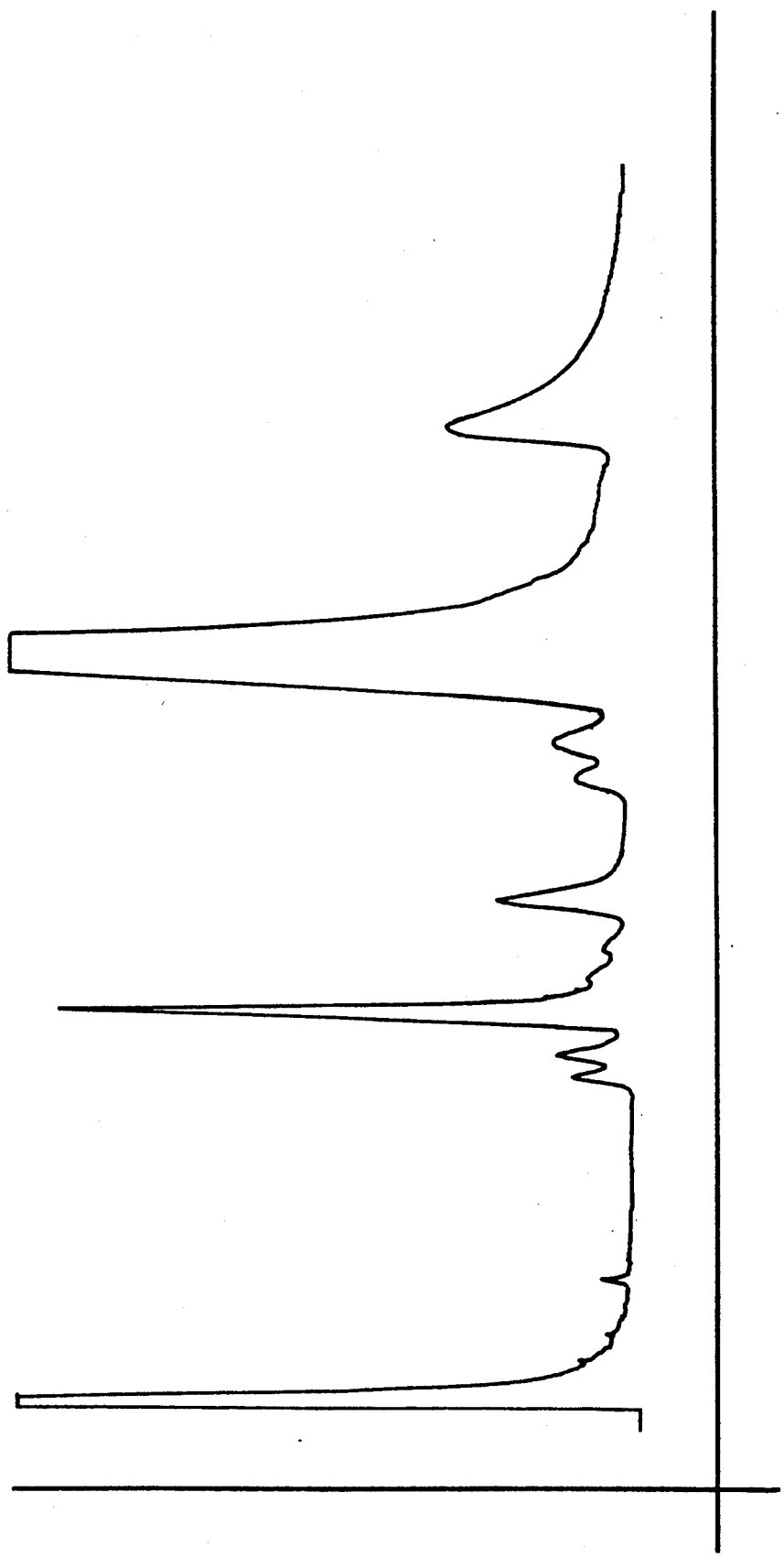

FIG. 2 is the GC spectrum for the crude reaction product of Example I containing the compound having the structure:

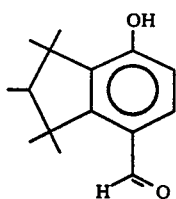

(Conditions: Carboxwax column programmed at 100°-220° C. at 8° C. per minute).

Figure 3:
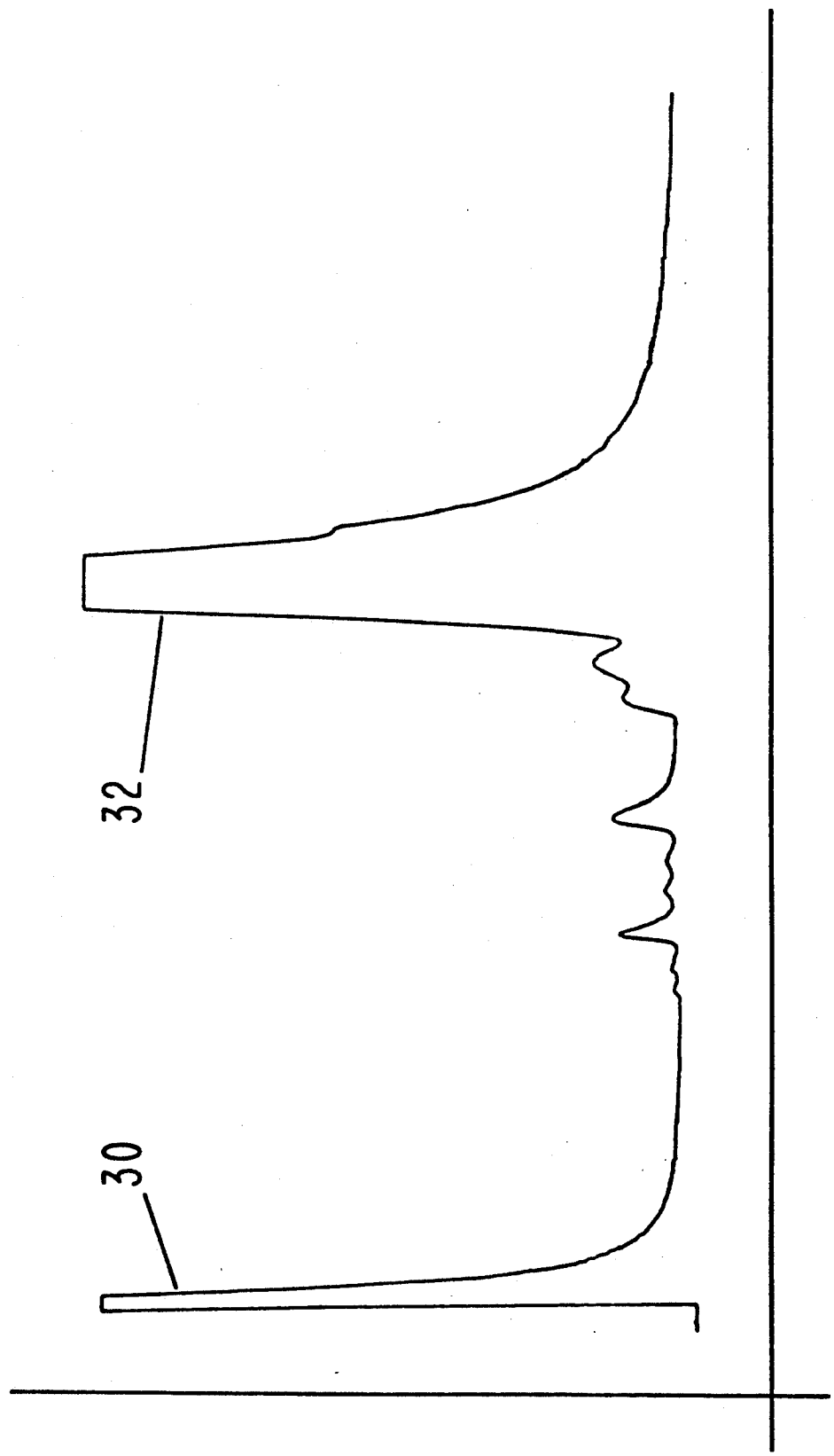

FIG. 3 is the GC spectrum for distillation fraction 3 of the distillation of the reaction product of Example I containing the compound having the structure:

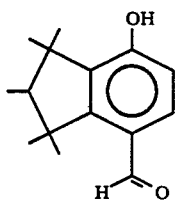

(Conditions: Carboxwax column programmed at 100°-220° C. at 8° C. per minute).

Figure 4:
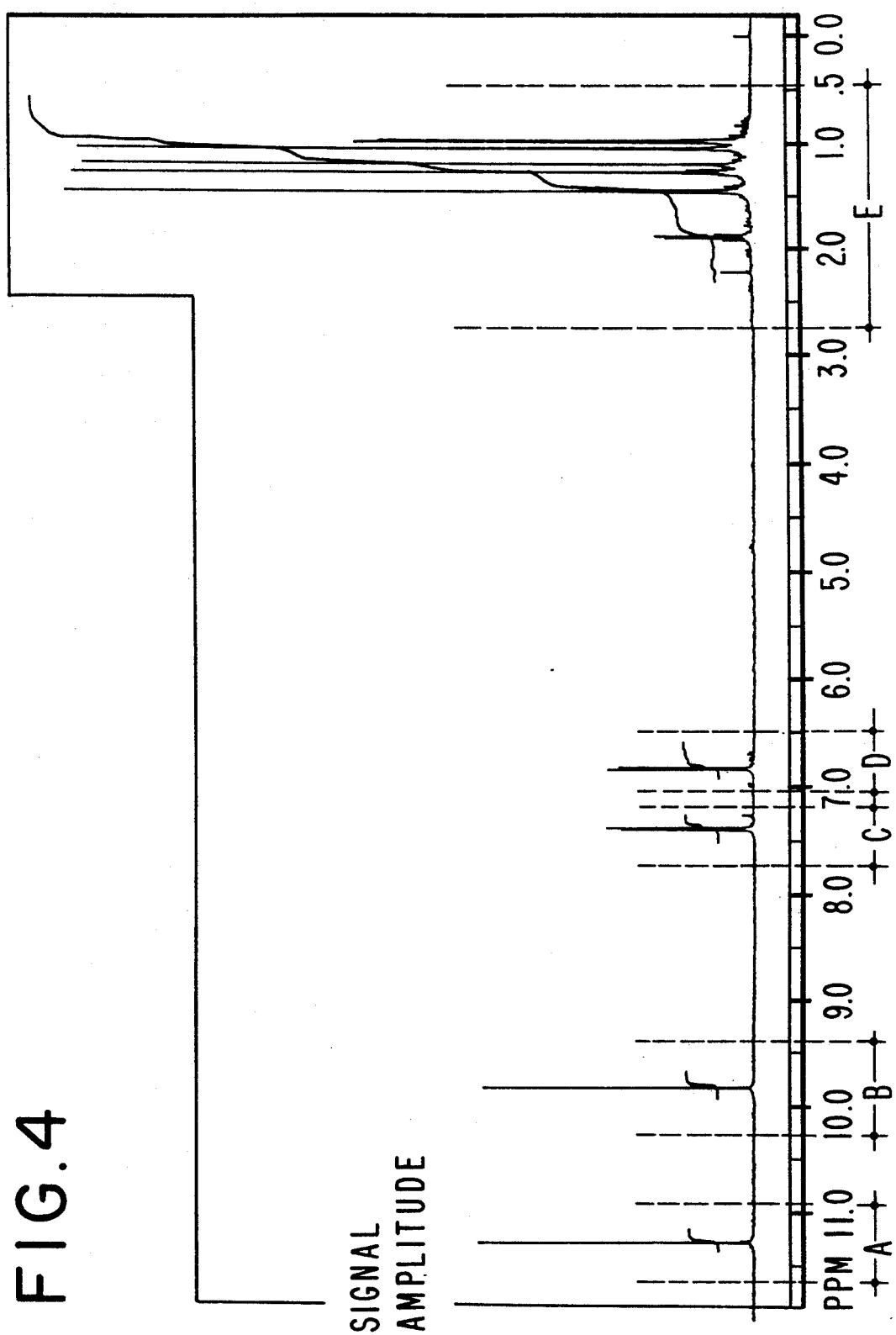

FIG. 4 is the NMR spectrum for the compound having the structure:

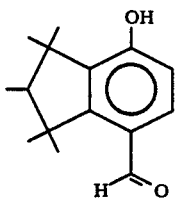

prepared according to Example I.

FIGS. 4A, 4B, 4C, 4D and 4E are enlargements of sections "A", "B", "C", "D" and "E" of the NMR spectrum of FIG. 4.

Figure 5:
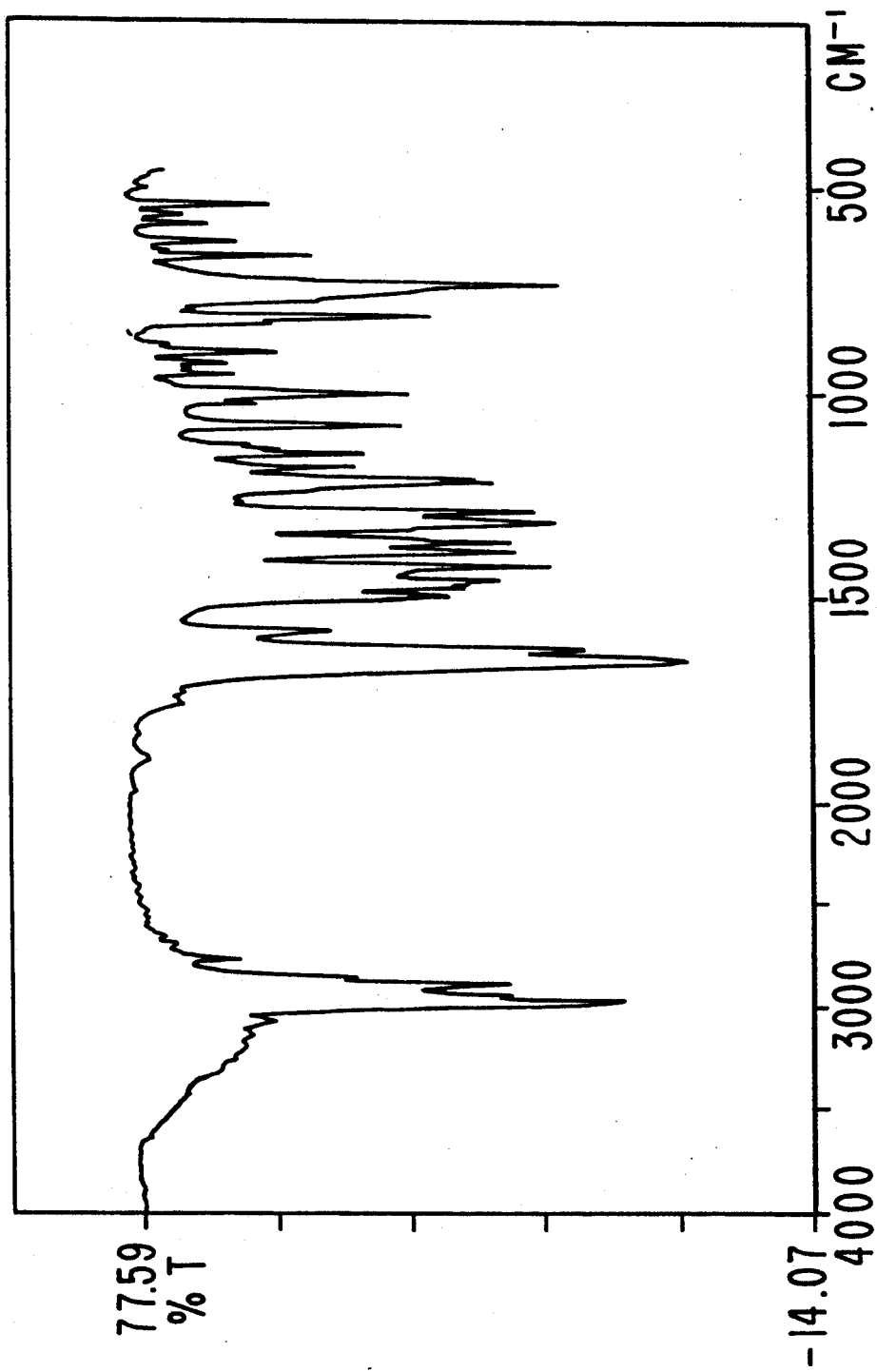

FIG. 5 is the infra-red spectrum for the compound having the structure:

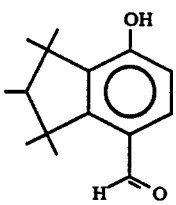

prepared according to Example I.

Figure 6:
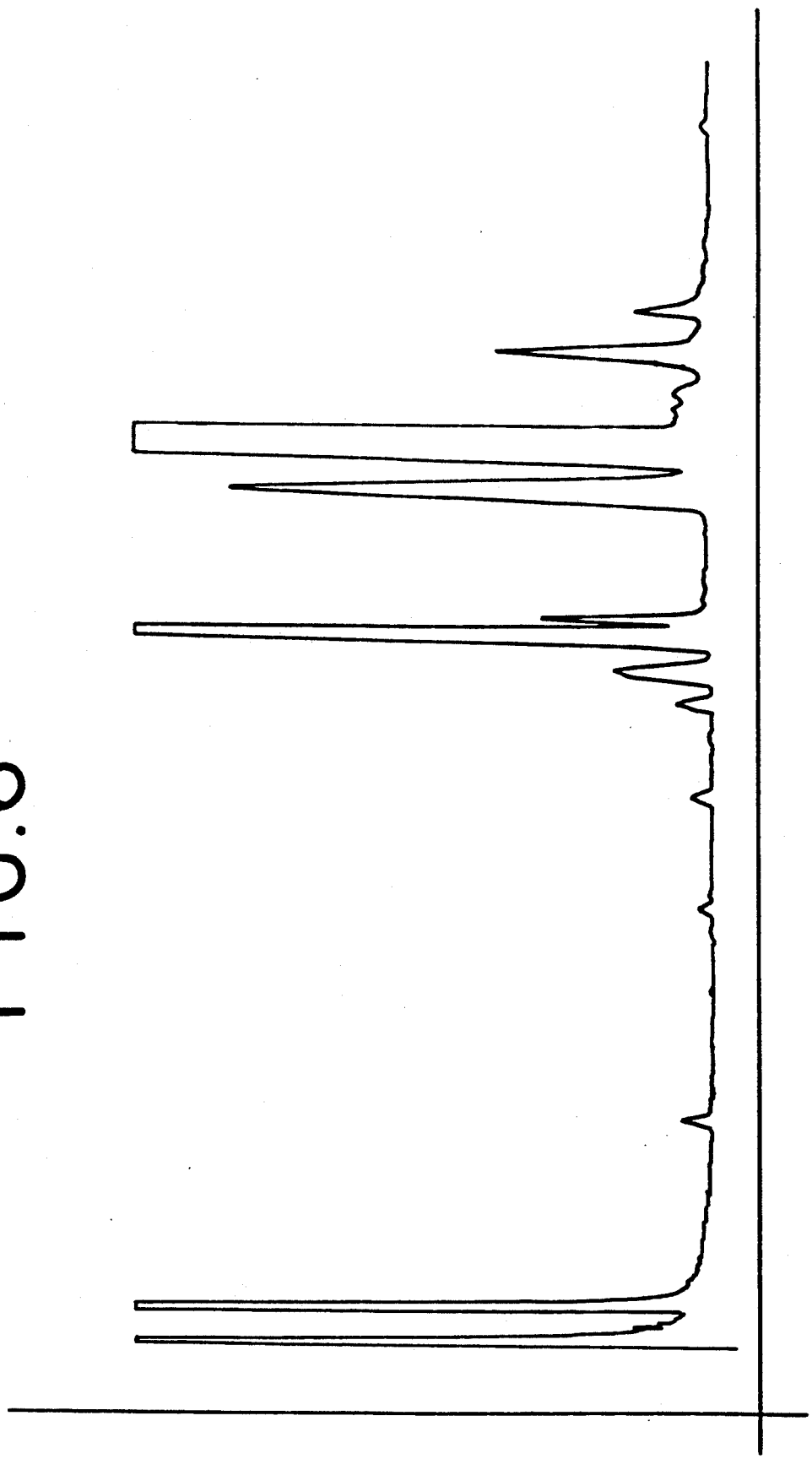

FIG. 6 is the GC spectrum for the crude reaction product of Example II containing the compound having the structure:

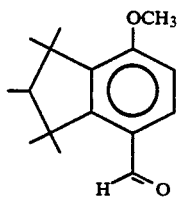

(Conditions: SE-30 column programmed at 100°-220° C. at 8° C. per minute).

Figure 7:
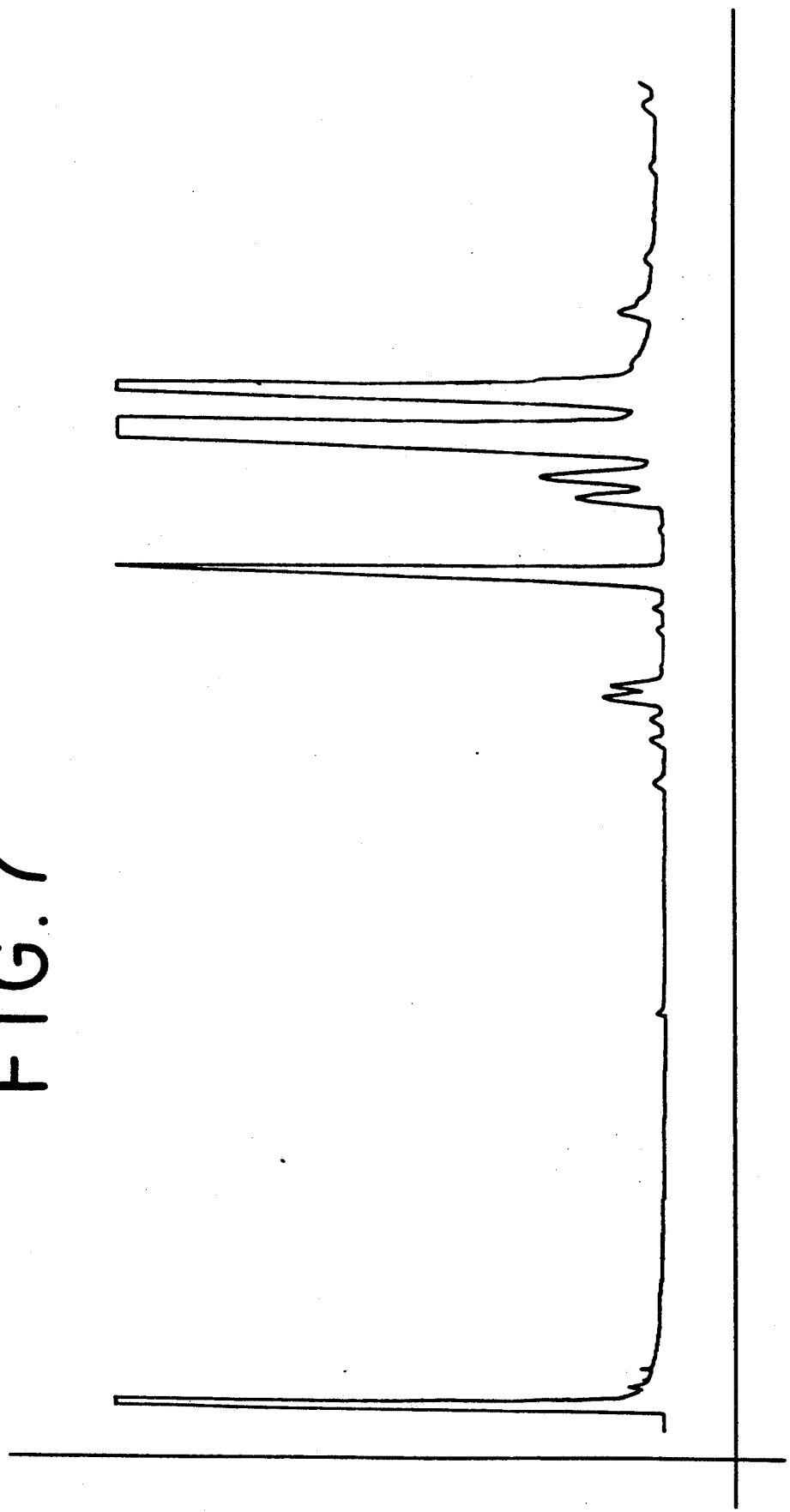

FIG. 7 is the GC spectrum for distillation fraction 3 for the distillation product of the reaction product of Example II containing the compound having the structure:

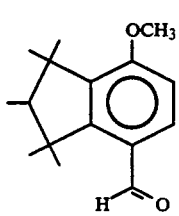

(Conditions: SE-30 column programmed at 100°-220° C. at 8° C. per minute).

Figure 8:
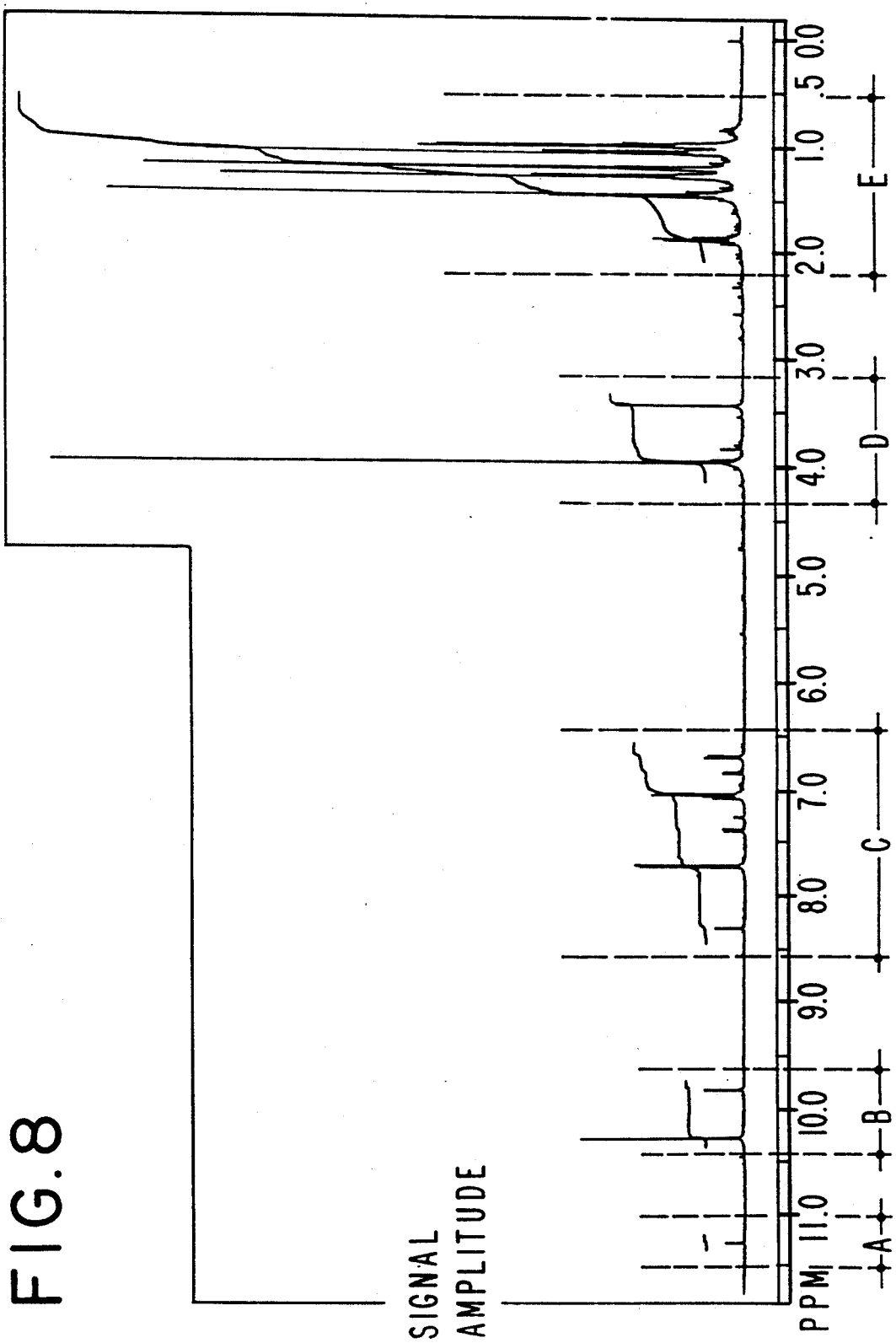

FIG. 8 is the NMR spectrum for the compound having the structure:

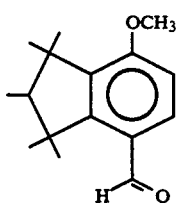

prepared according to Example II.

FIGS. 8A, 8B, 8C, 8D and 8E are enlargements of sections "A", "B", "C", "D" and "E" of the NMR spectrum of FIG. 8.

Figure 9:
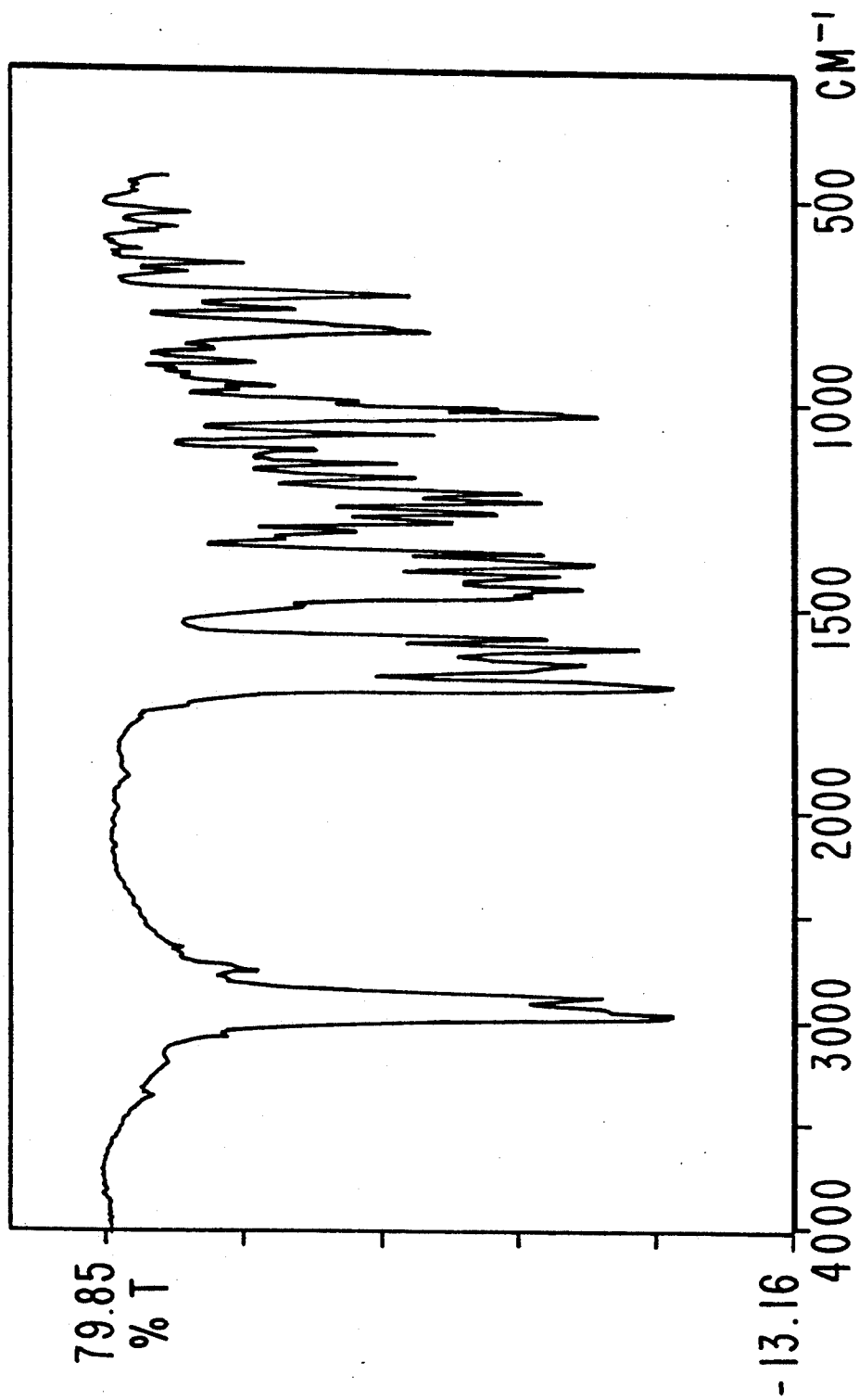

FIG. 9 is the infra-red spectrum for the compound having the structure:

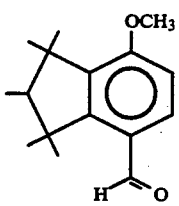

prepared according to Example II.

Figures 10, 11:
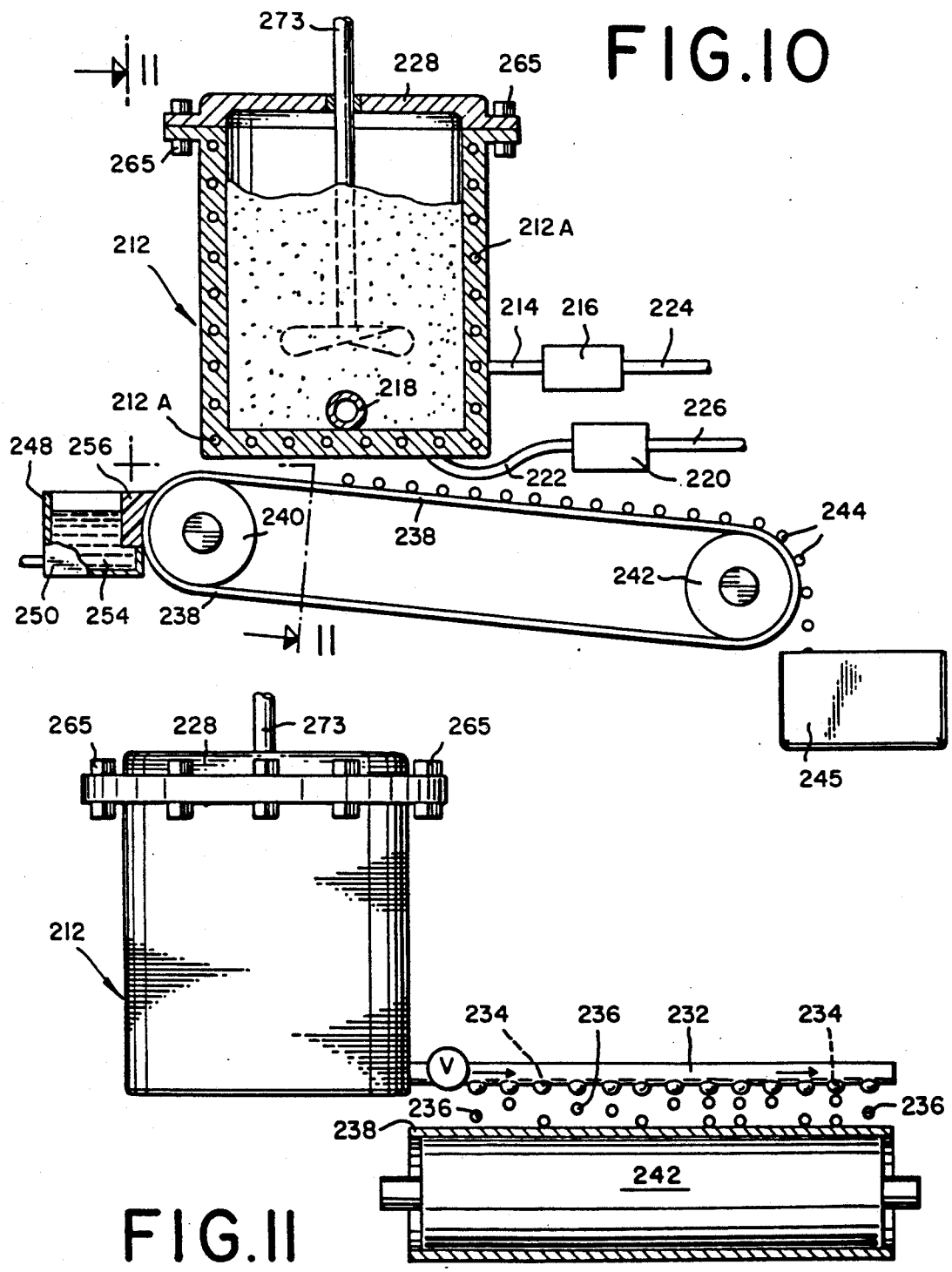

FIG. 10 is a partial side elevation and partial sectional view of an apparatus for forming scented polymer using at least one of the oxypentamethylindane carboxaldehydes of our invention.

FIG. 11 is a section taken along line 11—11 of FIG. 10.

FIG. 12A is a graph showing absorbency versus wavelength in the ultra-violet wave length range for the compound having the structure:

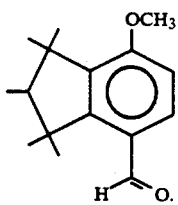

FIG. 12B is a graph showing ultra-violet absorbency versus wave length in the ultra-violet range for the compound having the structure:

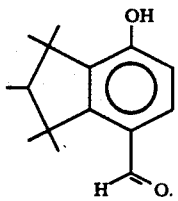

DETAILED DESCRIPTION OF THE DRAWINGS

FIG. 3 is the GC spectrum for distillation fraction 3 of the distillation product of the reaction product of Example I (Conditions: Carboxwax column programmed at 100°-220° C. at 8° C. per minute). The peak indicated by reference numeral 30 is the peak for the acetone solvent. The peak indicated by reference numeral 32 is the peak for the product having the structure:

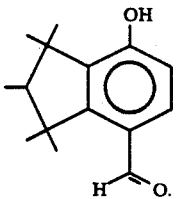

Referring to the drawings in FIGS. 10 and 11 in particular, the invention embodied therein comprises a device for forming scented polymer pellets (e.g., polyethylene, polypropylene of mixtures of polyepsilon caprolactone and polyethylene or polypropylene or co-polymers of polyvinyl acetate and polyethylene) which comprises a vat of container 210 into which a mixture of polymer such as polyethylene and at least one of the oxypentamethylindane carboxaldehydes of our invention or a mixture of perfume materials including as a key ingredient at least one of the oxypentamethylindane carboxaldehydes of our invention is placed.

The container is closed by an air-tight lid 228 and clamped to the container by clamps 265. A stirrer 273 traverses the lid or cover 228 in air-tight manner and is rotated in suitable manner. A surrounding cylinder 212 having heating coils which are supplied with electrical current through cable 214 from a rheostat and control 216 is operated to maintain the temperature inside the container such that the polymer such as polyethylene in the container will be maintained in a molten or liquid state. It has been found advantageous to employ a colorless, odorless polymer such as low density polyethylene with a viscosity ranging between 180 and 220 centistokes and having a melting point in the neighborhood of 220° F. The heater 212A is operated to maintain the upper portion of the container within a temperature range of from 250°-350° F. An additional bottom heater 218 is regulated through a control 220 connected thereto through a connecting wire 222 to maintain the lower portion of the container within a temperature range of from 250° to 350° F.

In accordance with this aspect of our invention, a polymer such as polyethylene or polypropylene is added to the container and is then heated from 10 to 12 hours whereafter a scent or aroma-imparting material containing at least one of the oxypentamethylindane carboxaldehydes of our invention is quickly added to the melt. The material must be compatible with the polymer and forms a homogeneous liquid melt therewith. The heat resisting material, generally about 10-40% by weight of the mixture containing the oxypentamethylindane carboxaldehydes of our invention is added to the polymer.

After the above mixture of perfumery chemicals containing or consisting of at least one of the oxypentamethylindane carboxaldehydes of our invention is added to the container, the mixture is stirred for a few minutes, for example 5 to 15 minutes, and maintained within the temperature range as indicated previously by heating coils 212A and 218 respectively. The controls 216 and 220 are connected through cables 224 and 226 to a suitable supply of electric current for supplying the power for heating purposes.

Thereafter the valve "V" is opened permitting the mass to flow outwardly through a conduit 232 having a multiplicity of orifices 234 adjacent the lower side thereof. The outer end of the conduit 232 is closed so that the liquid polymer and perfumery chemical mixture will continuously drop through the orifices 234 downwardly from the conduit 232. During this time the temperature of the polymer and the composition containing at least one of the oxypentamethylindane carboxaldehydes of our invention in the container is accurately controlled so that a temperature in the range of from 210° F. up to 275° F. will cause such composition to exit in the conduit 232. The regulation of the temperature through the control 216 and the control 220 is essential in order to insure temperature balance to provide for the continuous dropping or dripping of molten polymer and composition containing at least one of the oxypentamethylindane carboxaldehydes of our invention through the orifices 234 at a range which will insure the formation of droplets 236 which will fall downwardly onto a moving conveyor belt 238 trained to run between conveyor wheels 240 and 242 beneath the conduit 232. When the droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets 244 are then collected from the container 246 and packaged for shipment.

A feature of the invention is the provision for moistening of the conveyor belt 238 to insure the rapid formation of the solid polymer scented pellets 244 without sticking to the belt. The belt 238 is advantageously of a material which will not normally stick to a melted polymer but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

Referring to 12A, a graph of UV absorbency versus wave length (nm) for the compound having the structure:

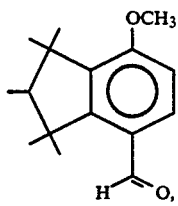

the peak indicated by reference numeral 122 is the peak for the maximum absorbency at 214 nm. The peak indicated by reference numeral 124 is the peak for maximum absorbency at a wave length of 265 nm. The peak indicated by reference numeral 126 is the peak for maximum absorbency at a wave length of 310 nm. The "epsilon" values for these peaks are as follows:

$\epsilon_{214} = 1.973 \times 10^4$ $\epsilon_{268} = 1.45833 \; 10^4$ $\epsilon_{310} = 1.798 \times 10^3$ Referring to FIG. 12B, the graph of UV absorbence versus wave length (nm) for the compound having the structure:

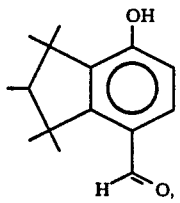

the peak indicated by reference numeral 121 is the peak for the maximum absorbence at 217 nm; the peak indicated by reference numeral 123 is the peak for the maximum absorbence at 270 nm. The peak indicated by reference numeral 125 is the peak for the maximum absorbence at 331 nm wave length. The epsilon values for these three peaks are as follows:

$\epsilon_{217} = 2.1019 \times 10^4$ $\epsilon_{270} = 1.632 \times 10^4$ $\epsilon_{331} = 2.930 \times 10^3$ The conditions for the data set forth in FIG. 12A are as follows:
Sample weight = 0.0771 grams
Path length = 1 cm
Concentration (M/L) = $2.5032 \times 10^{-5}$.

Conditions for obtention of the data in FIG. 12B are as follows:
Sample weight = 0.0575 grams
Path length = 1 cm
Concentration (M/L) = $1.9792 \times 10^{-5}$.

THE INVENTION

It has now been discovered that novel perfume compositions and perfumes as well as perfumed articles having high ultra-violet light absorbency and having extended long-lasting and highly intense musky, woody, rose, herbaceous and sweet aromas with leathery undertones may be provided by utilization of at least one of the oxypentamethylindane carboxaldehydes defined according to the generic structure:

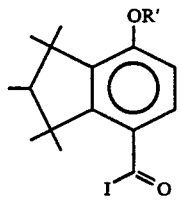

wherein R' represents hydrogen or methyl.

The oxypentamethylindane carboxaldehydes of our invention may be prepared by utilizing the starting material having the structure:

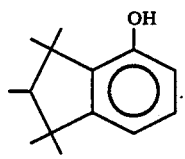

The compound having the structure:

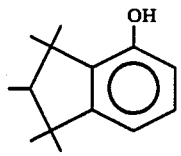

is reacted with formaldehyde or a source thereof such as hexamethylenetetramine according to the generic reaction:

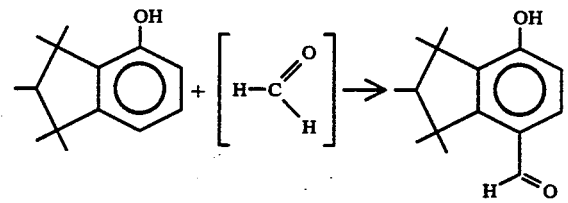

or the specific reaction using hexamethylenetetramine, to wit:

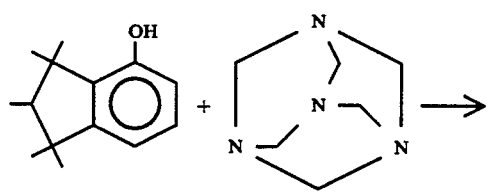

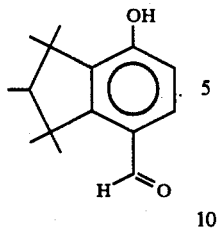

The resulting compound having the structure:

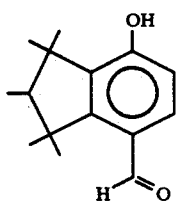

may be used "as is" for its perfumery properties or its ultra-violet absorbency properties or both or the compound having the structure:

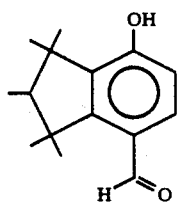

may further be reacted with an etherifying agent such as dimethyl sulfate according to the reaction:

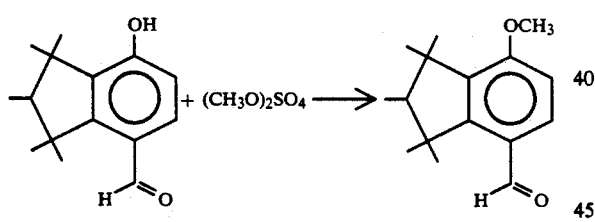

to produce the compound having the structure:

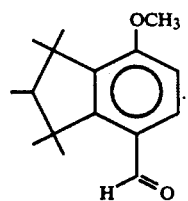

Each of the compounds having the structures:

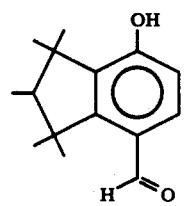

and

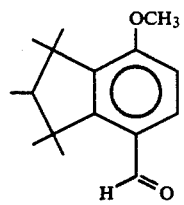

subsequent to their preparation may be purified as by fractional distillation.

Referring to the reaction:

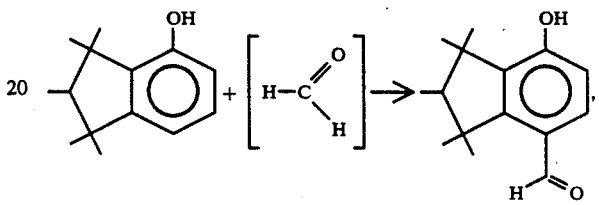

the reaction is preferably carried out using hexamethylenetetramine as a formaldehyde source in the presence of a weak acid such as acetic acid and strong acid such as hydrochloric acid. The reaction is carried out preferably at a temperature in the range of from about 80° up to about 100° C. for a period of time of from about one hour up to about three hours. The compound having the structure:

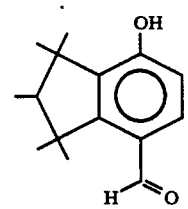

is then fractionally distilled after "work up" at a temperature of from about 125° C. up to about 140° C. at a vacuum of from about 2.0 mm/Hg. up to about 3.0 mm/Hg.

The resulting product is then used as is for its perfumery properties or may then be further reacted with an etherifying agent such as dimethyl sulfate.

Referring to the reaction, to wit:

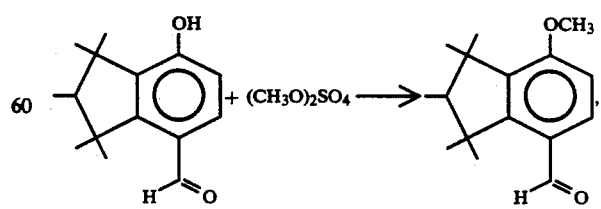

this reaction takes place in the presence of an inert solvent such as toluene, with the mole ratio of dimethyl sulfate:compound having the structure:

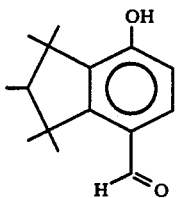

varying from about 0.5:1 up to about 1:1. At the end of the reaction either the entire material is etherified to form the compound having the structure:

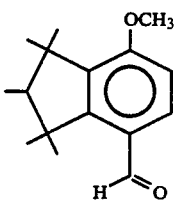

or a mixture of compounds is produced having the structures:

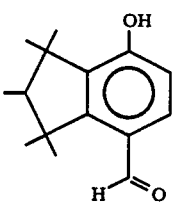

and

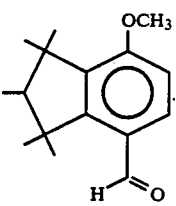

The etherification reaction is carried out at a temperature in the range of from about 100°–110° C. at reflux conditions for a period of from about one hour up to about three hours. At the end of the reaction, the reaction mass is "worked up" and the resulting product is fractionally distilled at a temperature of from about 130° up to about 140° C. and a vacuum of about 3.0 mm/Hg.

The following table sets forth the perfumery properties and structures of the reaction products, the oxypentamethylindane carboxaldehydes of our invention:

TABLE I

| Structure of Material | Perfumery Properties |
|---|---|
| The compound having the structure: | A musky, woody and rose aroma with leathery undertones. |

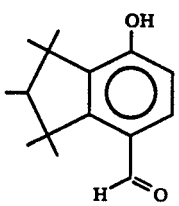

TABLE I-continued

| Structure of Material | Perfumery Properties |
|---|---|
| prepared according to Example I. The compound having the structure: | A woody, musky, herbaceous and sweet aroma. | prepared according to Example II.

When the oxypentamethylindane carboxaldehydes of our invention are used as perfume aroma adjuvants, the nature of the co-ingredients included with said oxypentamethylindane carboxaldehydes will also serve to alter the organoleptic characteristics of any ultimate perfumed article treated therewith.

As used herein the terms "alter" and "modify" in their various forms mean supplying or imparting a perfume aroma character or note to otherwise bland substances or augmenting the existing aroma characteristics where natural aroma is deficient in some regard or supplementing the existing aroma impression to modify its quality, character or aroma.

As used herein the term "enhance" is intended to mean the intensification (without effecting a change in kind or quality of aroma) of one or more aroma nuances and their organoleptic impression of a perfume, perfume composition or one or more perfumed articles.

The oxypentamethylindane carboxaldehydes of our invention and one or more auxiliary perfume ingredients including, for example, alcohols (other than the alcohols of our invention), aldehydes (other than the aldehydes of our invention), ketones, nitriles, esters, lactones, natural essential oils, synthetic essential oils and mercaptans may be admixed so that the combined odors of the individual components produce a pleasant and desired fragrance, particularly and perferably in the rose and musk fragrance area.

It is to be understood that such additional adjuvants are to be organoleptically compatible with each of the oxypentamethylindane carboxaldehydes of our invention and further that such adjuvants are to be non-reactive under use conditions at room temperature and storage conditions with the oxypentamethylindane carboxaldehydes of our invention.

Such perfume compositions usually contain (a) the main note or bouquet or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

It is the individual components which will contribute their particular olfactory characteristics; and these individual components will also alter, modify or enhance the overall effect of the perfume composition. Thus, the oxypentamethylindane carboxaldehydes of our invention taken alone or in combination can be used to alter, augment or enhance the aroma characteristics of a perfume composition, for example, by utilizing or moderating the olfactory reaction contributed by one or more other ingredients in the composition.

The amount of oxypentamethylindane carboxaldehydes of our invention which will be effective in the perfume composition depends on many factors including the other ingredients, their amounts and the effects which are desired. It has been found that perfume compositions containing as little as 0.1% of the oxypentamethylindane carboxaldehydes of our invention can be used to impart, augment or enhance long-lasting and intense musky, woody, rose, herbaceous and sweet aromas with leathery undertones to cosmetics and other products including fabric softening articles used in clothes driers, solid or liquid anionic, cationic, nonionic or zwitterionic detergents and perfumed polymers. The amount employed can range up to 75% by weight of the fragrance components and will depend on considerations of cost, nature of the end product and effect desired on the finished product and the particular fragrance sought. Uniquely, the oxypentamethylindane carboxaldehydes of our invention also provide ultraviolet light absorbency and accordingly, can be used simultaneously as ultra-violet absorbers as well as perfumants in sun screen compositions.

One or more of the oxypentamethylindane carboxaldehydes of our invention are useful taken alone or in perfume compositions as olfactory components in anionic, cationic, nonionic or zwitterionic detergents.

On or more of the oxypentamethylindane carboxaldehydes of our invention are also useful as perfumants taken together with other perfumery materials in soaps, space odorants and deodorants, colognes, toilet water, bath preparations such as bath oils and bath solids, hair preparations such as lacquers, brilliantines, pomades and shampoos; cosmetic preparations such as creams, deodorants, hand lotions and sun screens (as stated, supra); powders such as talcs, dusting powders and face powders; perfumed polymers; insect repellents; animal repellents; and insect and animal pheromones. When used as an olfactory component, as little as 0.025% of one or more of the oxypentamethylindane carboxaldehydes of our invention will suffice to impart musky, woody, rose, herbaceous and sweet aromas with leathery undertones to rose or musk formulations. Generally no more than 3% of the oxypentamethylindane carboxaldehydes of our invention based on the ultimate end product is required in the perfumed article. Accordingly, the range of the oxypentamethylindane carboxaldehydes of our invention in the perfumed article may vary from about 0.025% up to about 3% by weight of the perfumed article.

In addition, the perfume composition or fragrance composition of our invention can contain a vehicle or carrier for the oxypentamethylindane carboxaldehydes of our invention. The vehicle can be a liquid such as a non-toxic alcohol (e.g., 95% food grade ethanol), a non-toxic glycol (e.g., propylene glycol) or the like. The carrier can also be an absorbent solid such gum (e.g., gum arabic, xanthan gum or guar gum or mixtures of same) or components for encapsulating the composition (such as gelatin as by means of coacervation) or such as a urea formaldehyde prepolymer for formation of a urea formaldehyde polymer around a liquid perfume center.

More specifically, the oxypentamethylindane carboxaldehydes of our invention may be blended into polymers when forming a perfumed polymer by means of extrusion using a single or double screw extruder or technique such as that set forth in U.S. Pat. No. 4,247,498 issued on Jan. 27, 1981 (the specification for which is incorporated herein by reference) which discloses microporous polymers which are capable of containing volatile substances such as perfumes and the like in forms ranging from films to blocks and intricate shapes from synthetic thermoplastic polymers such as olefinic condensation or oxidation polymers. Other techniques of blending the oxypentamethylindane carboxaldehydes of our invention with polymers are exemplified in U.S. Pat. No. 3,505,432 (the specification for which is incorporated by reference herein) which discloses a method for scenting polyolefin with such materials as the oxypentamethylindane carboxaldehydes of our invention which process comprises:

(a) mixing a first amount of the liquid polyolefin (e.g., polyethylene or polypropylene) with a relatively large amount of scent-imparting material (in this case at least one of the oxypentamethylindane carboxaldehydes of our invention) to form a flowable mass;

(b) forming drops of said mass and causing substantially instantaneous solidification of said drops into polyolefin pellets having a relatively large amount of such scent-imparting materials as at least one of the oxypentamethylindane carboxaldehydes of our invention imprisoned therein;

(c) melting said pellets with a second amount of polyolefin with said second amount being larger than said first amount; and (d) solidifying the melt of (c).

The following Examples I and II serve to illustrate a method for preparing at least one of the oxypentamethylindane carboxaldehydes of our invention. The following Examples III, et seq. serve to illustrate the organoleptic utilities and ultra-violet absorbency utilities of products of our invention. This invention is to be considered restricted to the examples only as indicated in the appended claims.

All parts and percentages given herein are by weight unless otherwise specified.

EXAMPLE I

Preparation of
7-Hydroxy-1,1,2,3,3-Pentamethyl-4-Indancarboxaldehyde

Reaction:

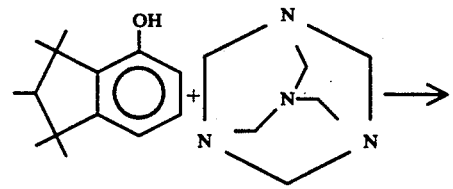

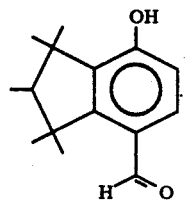

Into a 5 liter reaction vessel equipped with stirrer, thermometer, reflux condenser and heating mantle are placed 1000 grams (4.90 moles) of the compound having the structure:

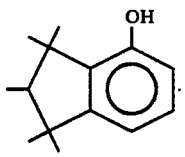

Over a period of five minutes, 700 grams (4.90 moles) of hexamethylenetetramine is added to the reaction mass.

Over a period of five minutes, a mixture of 300 cc of acetic acid and 1000 cc of concentrated hydrochloric acid is added to the reaction mass.

The reaction mass is heated to 85°–90° C. and maintained at 85°–90° C. for a period of two hours.

At the end of the two hour period, the reaction mass is cooled and neutralized to pH=7 with a saturated aqueous solution of sodium bicarbonate. The reaction mass now exists in two phases. The organic phase is separated from the aqueous phase. The organic phase is admixed with 2000 cc of water and the resulting mixture is heated at 100°–105° C. at reflux for a period of three hours. The resulting mixture is then cooled to room temperature and the organic phase is separated from the aqueous phase. The organic phase is washed with one 2000 cc portion of water and then fractionally distilled yielding the following fractions:

| Fraction No. | Vapor Temp. (°C.) | Liquid Temp. (°C.) | Vacuum mm/Hg. Pressure |
|---|---|---|---|
| 1 | 125/135 | 145/150 | 2.0/2.0 |
| 2 | 140 | 165 | 2.5 |
| 3 | 140 | 195 | 2.8. |

The resulting product has the structure:

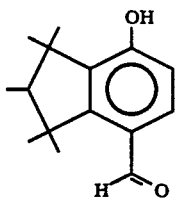

The resulting product has a musky, woody and rose aroma with leathery undertones. The products structure is identified by means of NMR and IR analyses as shown in FIGS. 4 and 5.

EXAMPLE II

Preparation of 7-Methoxy-1,1,2,3,3-Pentamethyl-4-Indancarboxaldehyde

Reaction:

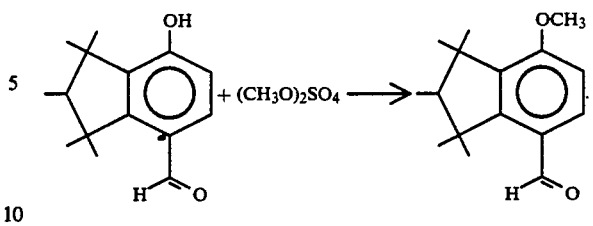

Into a 2 liter reaction vessel equipped with stirrer, thermometer, reflux condenser and heating mantle is placed a mixture of 232 grams of the compound having the structure:

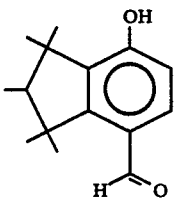

prepared according to Example I and 500 cc of toluene. Over a period of 10 minutes, 126 grams (1 mole) of dimethyl sulfate is added to the reaction mass. Over a period of 10 minutes, 80 grams (1 mole) of 50% aqueous sodium hydroxide solution is added, dropwise, to the reaction mass.

At the end of the addition of the reactants to the reaction mass, the reaction mass is heated to reflux (105° C. and maintained at reflux for a period of two hours (105° C.). At the end of the two hour reaction period, the reaction mass is cooled to room temperature and 500 cc of water is added.

The reaction mass now exists in two phases; an organic phase and an aqueous phase. The organic phase is separated from the aqueous phase and washed with two 500 cc portions of water. The resulting product is then fractionally distilled yielding the following fractions:

| Fraction No. | Vapor Temp. (°C.) | Liquid Temp. (°C.) | Vacuum mm/Hg. Pressure |
|---|---|---|---|
| 1 | 120/130 | 140/145 | 3.0/3.0 |
| 2 | 140 | 160 | 3.0 |
| 3 | 140 | 180 | 3.0. |

The resulting product has the structure:

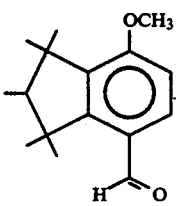

The compound having the structure:

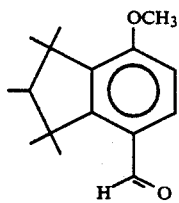

has a woody, musky, herbaceous and sweet aroma. The structure of the compound having the structure:

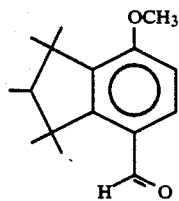

is confirmed by NMR and IR analyses as set forth in FIGS. 8 and 9, described, supra.

EXAMPLE III

Rose Formulations

The following mixtures are prepared:

| Ingredients | Parts by Weight | | |
|---|---|---|---|
| | III(A) | III(B) | III(C) |
| Rhodinol | 270.0 | 270.0 | 270.0 |
| Nerol | 90.0 | 90.0 | 90.0 |
| Linalool | 30.0 | 30.0 | 30.0 |
| Terpineol | 30.0 | 30.0 | 30.0 |
| Phenyl Ethyl Alcohol | 12.0 | 12.0 | 12.0 |
| Terpinenol | 5.0 | 5.0 | 5.0 |
| Linalyl acetate | 1.5 | 1.5 | 1.5 |
| Citronellyl acetate | 15.0 | 15.0 | 15.0 |
| Geranyl acetate | 10.0 | 10.0 | 10.0 |
| Eugenol | 33.0 | 33.0 | 33.0 |
| Citral | 15.0 | 15.0 | 15.0 |
| Phenyl Ethyl Acetate | 20.0 | 20.0 | 20.0 |
| Rose oxide | 8.0 | 8.0 | 8.0 |
| Guaiacol | 30.0 | 30.0 | 30.0 |
| l-Citronellal | 90.0 | 90.0 | 90.0 |
| Neryl acetate | 3.0 | 3.0 | 3.0 |
| Clove bud oil | 1.0 | 1.0 | 1.0 |
| Cadinene | 2.0 | 2.0 | 2.0 |
| Guaiene | 1.0 | 1.0 | 1.0 |
| Gum turpentine | 12.0 | 12.0 | 12.0 |
| Alpha-pinene | 1.0 | 1.0 | 1.0 |
| Myrcene | 5.0 | 5.0 | 5.0 |
| Limonene | 2.0 | 2.0 | 2.0 |
| p-Cymene | 1.0 | 1.0 | 1.0 |
| The compound having the structure: 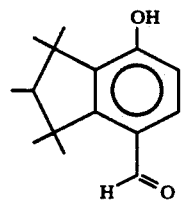 prepared according to Example I. | 45.0 | 0 | 0 |
| The compound having the structure: 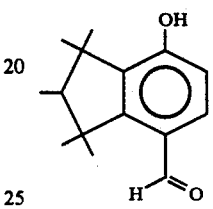 prepared according to Example II. | 0 | 45.0 | 0 |
| 50:50 Mixture of compounds having the structures: 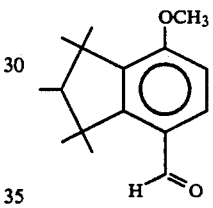 and 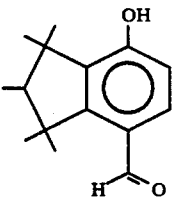 | 0 | 0 | 4.50 |

The compound having the structure:

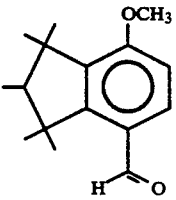

prepared according to Example I imparts to this rose formulation musky, woody and leathery undertones. Accordingly, the perfume composition of Example III(A) can be described as having "a rose aroma with musky, woody and leathery undertones".

The compound having the structure:

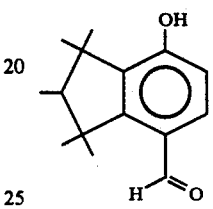

produced according to Example II imparts to this rose formulation woody, musky, herbaceous and sweet undertones. Accordingly, the rose formulation of Example III(B) can be described as having "a rose aroma with woody, musky, herbaceous and sweet undertones".

The mixtures of compounds having the structures:

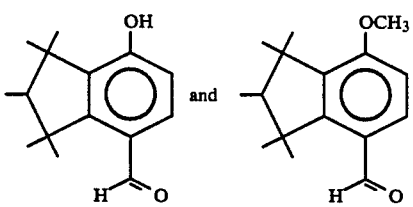

imparts to this rose formulation musky, woody, herbaceous, sweet and leathery undertones. Accordingly, the rose formulation of Example III(C) can be described as having "a rose aroma with musky, woody, herbaceous, sweet and leathery undertones".

EXAMPLE IV

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent as described in Table II below:

TABLE II

| Substance | Aroma Description |
|---|---|
| The compound having the structure:<br>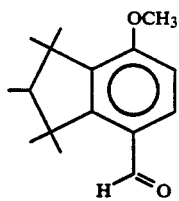<br>prepared according to Example I. | A musky, woody and rose aroma with leathery undertones. |
| The compound having the structure:<br>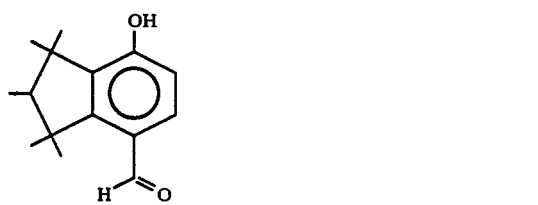<br>prepared according to Example II. | A woody, musky, herbaceous and sweet aroma. |
| 50:50 Mixture of compounds having the structure:<br>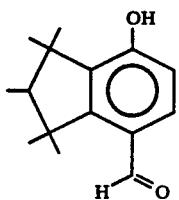<br>and | A musky, woody, rose, herbaceous and sweet aroma with leathery undertones. |

TABLE II-continued

| Substance | Aroma Description |
|---|---|
| Perfume formulation of Example III(A). | A rose aroma with musky, woody and leathery undertones. |
| Perfume formulation of Example III(B). | A rose aroma with woody, musky, herbaceous and sweet undertones. |
| Perfume formulation of Example III(C). | A rose aroma with musky, woody, herbaceous, sweet and leathery undertones. |

EXAMPLE V

Perfumed Liquid Detergent

Concentrated liquid detergents with aromas as set forth in Table II of Example IV (which detergents are prepared from Lysine salt of n-dodecyl benzene sulfonic acid as more specifically described in U.S. Pat. No. 3,948,818 issued on Apr. 6, 1976, the specification for which is incorporated by reference herein) are prepared containing each of the substances set forth in Table II of Example IV, supra. They are prepared by adding and homogeneously mixing the appropriate quantity of perfumery substance as set forth in Table II of Example IV in the liquid detergent. The detergents all possess aromas as set forth in Table II of Example IV, the intensity increasing with greater concentration of perfumery substance of Table II of Example IV, supra.

EXAMPLE VI

Preparation of a Cologne and Handkerchief Perfume

The perfume substances of Table II of Example IV, supra, are incorporated into colognes at concentrations of 1.5%, 2.0%, 2.5%, 3.0% and 4.0% in 80%, 85% and 90% aqueous ethanol; and into a handkerchief perfume composition at concentrations of 10%, 15%, 20%, 25% and 30% (in 85%, 90% and 95% aqueous ethanol). Distinct and definitive aromas as set forth in Table II of Example IV are imparted to the cologne and to the handkerchief perfume compositions.

EXAMPLE VII

Preparation of a Detergent Composition

A total of 100 grams of a detergent powder (a nonionic detergent powder containing a proteolytic enzyme prepared according to Example I of Canadian Patent No. 985,190 issued on Mar. 9, 1976, the disclosure of which is incorporated by reference herein) is mixed with 0.15 grams of each of the substances set forth in Table II of Example IV, supra, until substantially homogeneous compositions are obtained. These compositions have excellent aromas as set forth in Table II of Example IV.

EXAMPLE VIII

Preparation of Soap

Each of the perfumery substances of Table II of Example IV are incorporated into soap (LVU-1) at 0.1% by weight of each substance. After two weeks in the oven at 90° F. each of the soaps showed no visual effect from the heat. Each of the soaps manifested an excellent aroma as set forth in Table II of Example IV, supra.

EXAMPLE IX

Preparation of Soap Composition

One hundred grams of soap chips (IVORY ®, registered trademark of the Procter & Gamble Company of Cincinnati, Ohio) are mixed individually with one gram each of the perfumery substances of Table II of Example IV, supra, until a homogeneous composition is obtained. The homogeneous composition is then treated under three atmospheres pressure at 180° C. for a period of three ours and the resulting liquid is placed into a soap mold. The resulting soap cakes, on cooling manifest excellent aromas as set forth in Table II of Example IV, supra.

EXAMPLE X

Preparation of a Solid Detergent Composition

A detergent is prepared from the following ingredients according to Example I of Canadian Patent No. 1,007,948, the specification for which is incorporated by reference herein.

| Ingredients | Parts by Weight |
| --- | --- |
| "Neodol 45-11" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume substances of Table II of Example IV, supra. The detergent samples each have excellent aromas as set forth in Table II of Example IV, supra.

EXAMPLE XI

Utilizing the procedure of Example I at column 15 of U.S. Pat. No. 3,632,396 (the specification for which is incorporated by reference herein), a non-woven cloth substrate useful as a drier-added fabric softening article of manufacture is prepared, wherein the substrate, the substrate coating and the outer coating and the perfuming material are as follows:
1. a water "dissolvable" paper ("Dissolvo Paper");
2. Adogen 448 (m.p. about 140° F.) as the substrate coating; and
3. an outer coating having the following formulation (m.p. about 150° F.);
    57% —$C_{20-22}$ HAPS
    22% —isopropyl alcohol
    20% —antistatic agent
    1% —of one of the perfume substances of Table II of Example IV, supra.

A fabric softening composition prepared as set forth above having the above aroma characteristics as set forth in Table II of Example IV, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table II of Example IV is imparted in a pleasant manner to the headspace in the dryer on operation thereof, using said drier-added fabric softening non-woven fabric.

EXAMPLE XII

Ultra-Violet Absorbing Sun Screen Cream

The following cream is prepared:

| Ingredients | Grams |
| --- | --- |
| The compound having the structure: 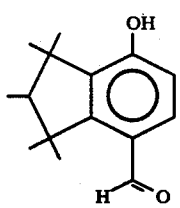 prepared according to Example I. | 3.00 |
| Sodium dodecyl sulfate | 0.80 |
| Glycerol | 2.00 |
| Stearyl alcohol | 20.00 |
| Triglycerides of capric/caprylic acids sold by Dynamit Nobel under the trade name "MIGLYOL ® 812" | 20.00 |
| Demineralized water | 54.20 |

The resulting product can be applied to the skin and gives rise to significant sun screen and perfume properties as a cream. The ulta-violet radiation absorbency on the skin can last up to six hours.

The 3.00 grams of the compound having the structure:

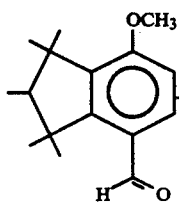

can be replaced by 3.00 grams of the compound having the structure:

with the same results. The 3.00 grams of the compound having the structure:

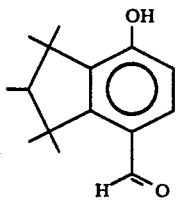

can be replaced with a mixture (50:50, weight:weight) of the compounds having the structures:

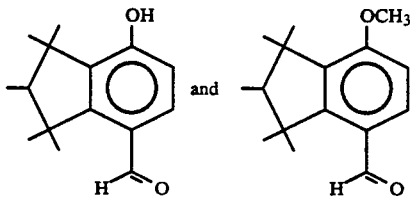

with same effect.

What is claimed is:

1. An oxypentamethylindane carboxaldehyde defined according to the structure:

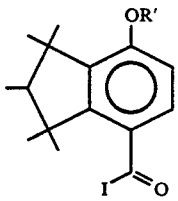

wherein R' is methyl or hydrogen.

2. The oxypentamethylindane carboxaldehyde of claim 1 having the structure:

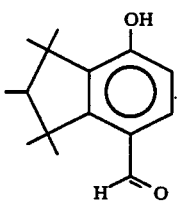

3. The oxypentamethylindane carboxaldehyde of claim 1 having the structure:

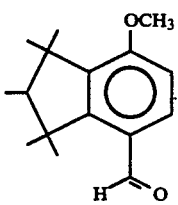

4. A process for imparting, augmenting or enhancing the aroma of a consumable material selected from the group consisting of perfume compositions, colognes and perfumed articles comprising the step of intimately admixing with said consumable material an aroma imparting, augmenting of enhancing quantity or concentration of the oxypentamethylindane carboxaldehyde defined according to claim 1.

5. The process of claim 4 wherein the oxypentamethylindane carboxaldehyde has the structure:

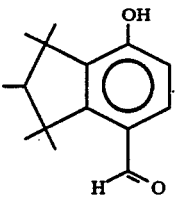

6. The process of claim 4 wherein the oxypentamethylindane carboxaldehyde has the structure:

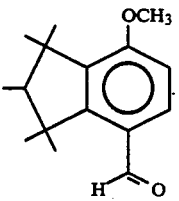

7. The process of claim 4 wherein the consumable material is a solid or liquid anionic, cationic, nonionic or zwitterionic detergent.

8. A perfume composition comprising a perfume base and intimately admixed therewith an aroma imparting, augmenting of enhancing quantity of at least one compound defined according to claim 1.

9. A perfumed article comprising a perfumed article base and intimately admixed therewith at least one oxypentamethylindane carboxaldehyde defined according to claim 1.

10. A perfumed polymer comprising a microporous polymer and contained in the interstices thereof at least one compound defined according to claim 1.

11. A sun screen cream having ultra-violet absorbency properties and having an aesthetically pleasing aroma comprising a cream base and intimately admixed therewith an aroma imparting, augmenting and enhancing quantity and an ultra-violet absorbent quantity of at least one compound defined according to claim 1.

12. The cream of claim 11 wherein the oxypentamethylindane carboxaldehyde has the structure:

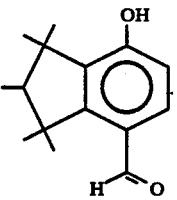

* * * * *